United States Patent
Fecher et al.

(10) Patent No.: US 10,105,200 B2
(45) Date of Patent: Oct. 23, 2018

(54) METHOD FOR PRODUCING A DENTAL MODEL AND CARRYING PLATE FOR RECEIVING SAME

(71) Applicant: DEGUDENT GMBH, Hanau (DE)

(72) Inventors: Stefan Fecher, Johannesberg (DE); Andreas Gebhardt, Langenselbold (DE); Martin Haizmann, Glauburg (DE); Heiner Horhold, Budingen (DE); Elmar Hock, Mombris (DE); Lothar Volkl, Goldbach (DE)

(73) Assignee: DEGUDENT GMBH, Hanau (DE)

( * ) Notice: Subject to any disclaimer, the term of this patent is extended or adjusted under 35 U.S.C. 154(b) by 513 days.

(21) Appl. No.: 14/368,056

(22) PCT Filed: Dec. 21, 2012

(86) PCT No.: PCT/EP2012/076598
§ 371 (c)(1),
(2) Date: Jul. 9, 2014

(87) PCT Pub. No.: WO2013/092980
PCT Pub. Date: Jun. 27, 2013

(65) Prior Publication Data
US 2015/0010880 A1    Jan. 8, 2015

(30) Foreign Application Priority Data
Dec. 23, 2011 (DE) .................. 10 2011 057 029

(51) Int. Cl.
*A61C 3/00*    (2006.01)
*A61C 13/00*   (2006.01)
(Continued)

(52) U.S. Cl.
CPC .......... *A61C 13/0027* (2013.01); *A61C 9/002* (2013.01); *A61C 9/004* (2013.01);
(Continued)

(58) Field of Classification Search
CPC .......... A61C 9/006; A61C 9/002; A61C 11/08; A61C 9/0093; A61C 13/0027; A61C 9/004; A61C 13/0004; A61C 13/34
(Continued)

(56) References Cited

U.S. PATENT DOCUMENTS 4,283,173 A * 8/1981 Browne .................. A61C 9/002
                                                  249/54
4,538,987 A * 9/1985 Weissman .............. A61C 9/002
                                                  249/54
(Continued)

FOREIGN PATENT DOCUMENTS

DE        19722989 C1    2/1999
DE     202004001768 U1   6/2005
(Continued)

OTHER PUBLICATIONS

German Search Report dated Dec. 13, 2012, corresponding to German Patent Application 102011057029.2.
(Continued)

*Primary Examiner* — Nicholas Lucchesi
(74) *Attorney, Agent, or Firm* — Ladas & Parry; Malcolm J. MacDonald

(57) ABSTRACT

The invention relates to a method for producing a dental model for removable insertion in a recess of a holder, which dental model has a referencing, comprising at least one tooth part having a base to be inserted into the recess, wherein the at least one tooth part is produced using digitized data of a jaw in that the digitized data are saved in a computer beforehand and supplied to a processing machine to produce the at least one tooth part. In order to ensure simple handling of the dental model and in particular to prevent faulty insertion of the dental model or segment, according to the invention the referencing is saved in the computer and, in (Continued)

Figure 1:
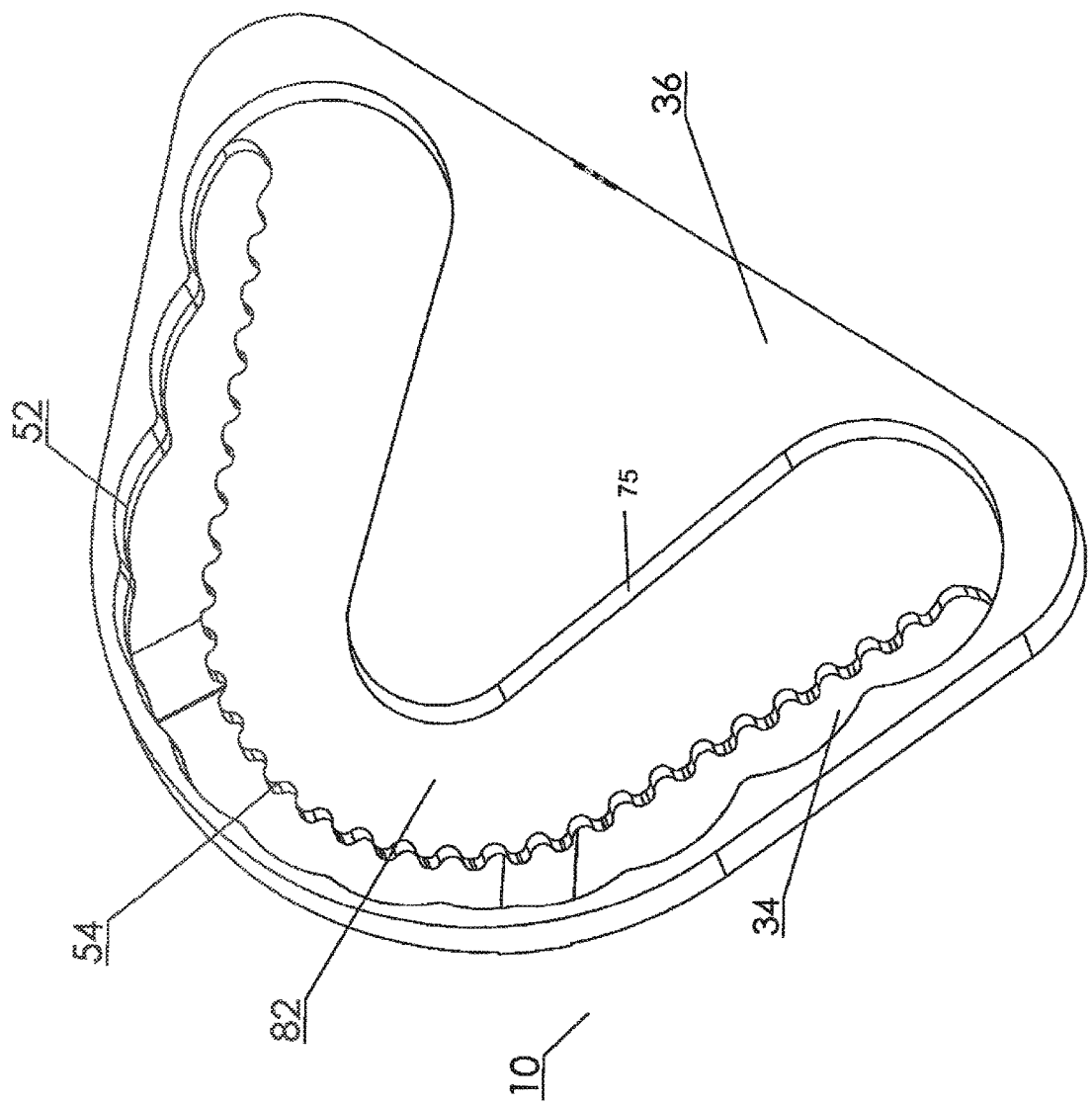

consideration of the referencing, the at least one tooth part is produced as having the base as a unit.

17 Claims, 11 Drawing Sheets

(51) Int. Cl.
  *A61C 9/00* (2006.01)
  *A61C 13/34* (2006.01)
  *A61C 11/08* (2006.01)
(52) U.S. Cl.
  CPC .......... *A61C 11/08* (2013.01); *A61C 13/0004* (2013.01); *A61C 13/34* (2013.01)
(58) Field of Classification Search
  USPC ............................ 433/34, 36, 37, 49, 60, 74
  See application file for complete search history.

(56) References Cited

U.S. PATENT DOCUMENTS

| | | | | |
|---|---|---|---|---|
| 4,608,016 A * | 8/1986 | Zeiser | ............... | A61C 9/002 433/60 |
| 4,671,769 A * | 6/1987 | Gill | ............... | A61C 9/002 433/213 |
| 4,708,648 A * | 11/1987 | Weissman | ............... | A61C 9/002 433/34 |
| 4,767,330 A * | 8/1988 | Burger | ............... | A61C 9/002 433/213 |
| 5,506,095 A * | 4/1996 | Callne | ............... | A61C 9/002 433/34 |
| 6,099,305 A * | 8/2000 | Browne | ............... | A61C 9/002 433/34 |
| 6,425,759 B1 * | 7/2002 | Cronin | ............... | A61C 9/002 433/34 |
| 6,537,066 B1 | 3/2003 | Azzaretto | | |
| 6,749,428 B2 * | 6/2004 | DiMarino | ............... | A61C 9/0006 433/37 |
| 2007/0072151 A1 | 3/2007 | Volkl et al. | | |
| 2008/0085489 A1 | 4/2008 | Schmitt | | |
| 2009/0208895 A1 * | 8/2009 | Lin | ............... | A61C 9/002 433/34 |
| 2010/0152873 A1 * | 6/2010 | Dunne | ............... | A61B 5/4547 700/98 |
| 2012/0052465 A1 | 3/2012 | Von Both et al. | | |
| 2013/0041630 A1 * | 2/2013 | Gilles | ............... | A61C 9/00 703/1 |

FOREIGN PATENT DOCUMENTS

| | | |
|---|---|---|
| DE | 102005009549 A1 | 10/2005 |
| DE | 102004054876 B3 | 7/2006 |
| EP | 0200193 A1 | 11/1986 |
| EP | 0 913 130 A2 | 5/1999 |
| EP | 1520551 A2 | 4/2005 |
| EP | 1 691 712 B1 | 8/2006 |
| FR | 2715826 A1 | 8/1995 |
| WO | 98/10709 A1 | 3/1998 |
| WO | 01/06945 A1 | 2/2001 |
| WO | 0239056 A1 | 5/2002 |
| WO | 2007/117239 A1 | 10/2007 |
| WO | 2008117323 A1 | 10/2008 |
| WO | 2010/099959 A1 | 9/2010 |
| WO | 2011103879 A1 | 9/2011 |

OTHER PUBLICATIONS

International Search Report dated Apr. 17, 2013, corresponding to International Patent Application PCT/EP2012/076598.
Espacenet English abstract of EP 0 913 130 A2.

* cited by examiner

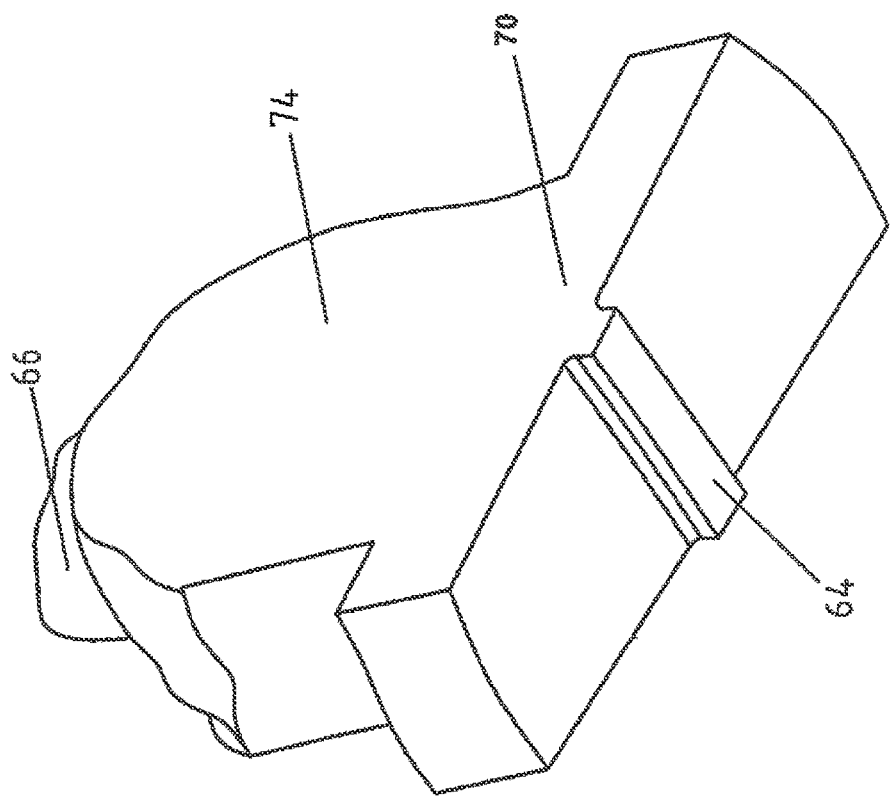

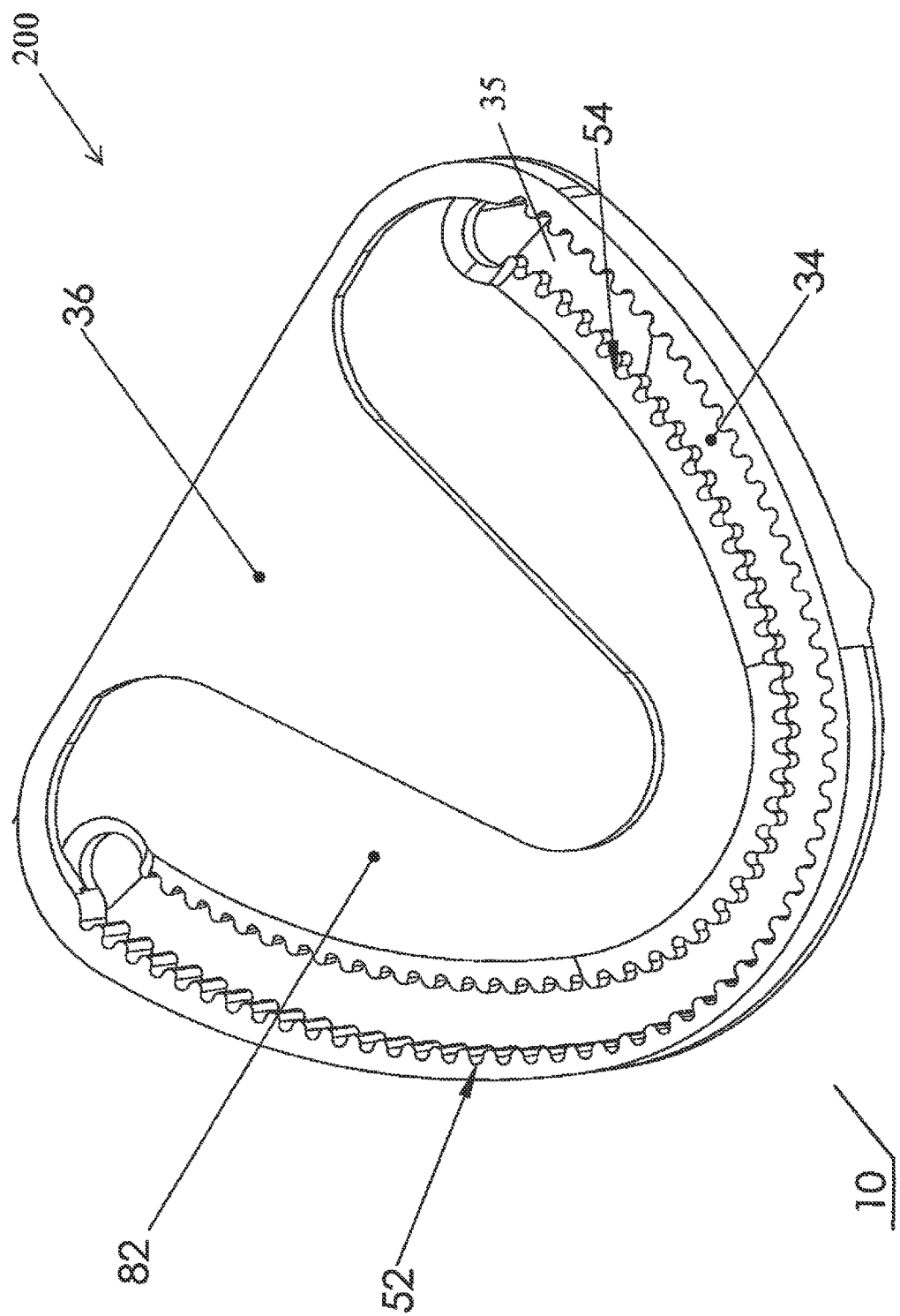

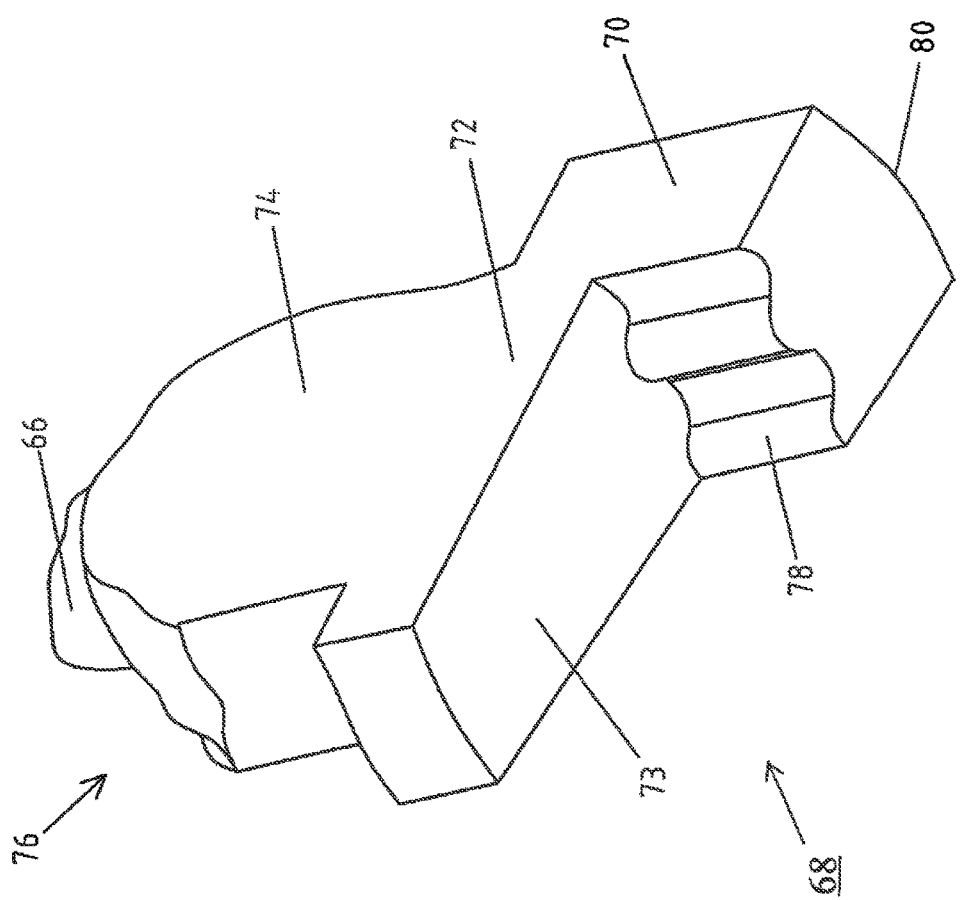

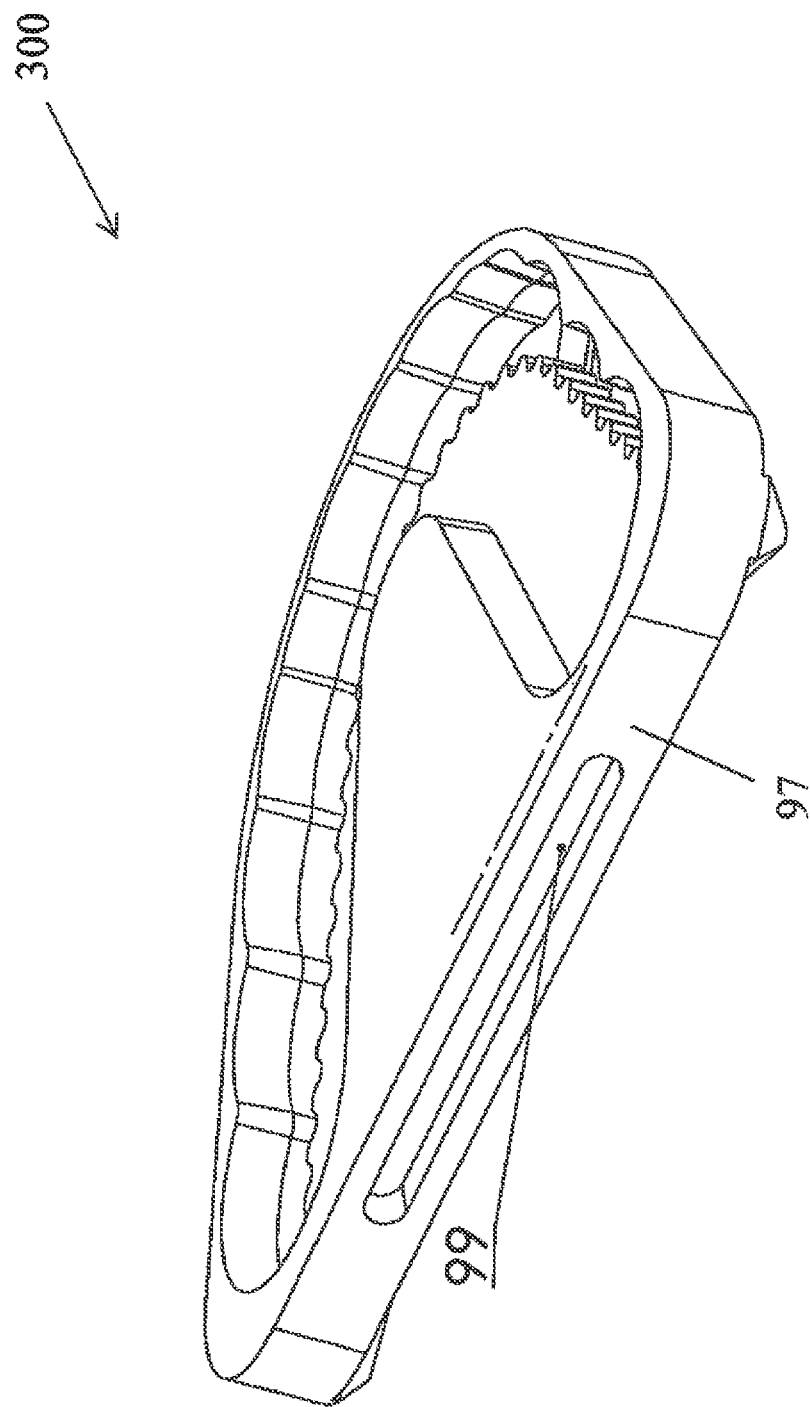

METHOD FOR PRODUCING A DENTAL MODEL AND CARRYING PLATE FOR RECEIVING SAME

This application is a 371 of PCT/EP2012/076598, filed on Dec. 21, 2012, which claims priority to German Application No. 102011057029.2 filed Dec. 23, 2011.

The invention relates to a method for producing a dental model for removable insertion in a recess of a holder which has a referencing, wherein the recess has a referencing and the model comprises at least one tooth part with a base, which is to be inserted in the recess, and wherein, using digitized data of a jaw or of a section thereof, the at least one tooth part is produced, in that the digitized data are saved beforehand in a computer, and with the use thereof they are supplied to a processing machine to produce the at least the one tooth part.

The invention further relates to a carrying plate for receiving a denture model or a segment or several segments of such a denture model, wherein the denture model or the at least one segment comprises a base with a tooth part or several tooth parts, and wherein the carrying plate has an upper face and a lower face and a cut-out with side surfaces extending along an arc, in the manner of a denture arch, side surfaces of which at least one, preferably both, has/have a referencing which forms a first guide for the base.

Another subject matter of the invention is a dental device comprising a dental model, consisting preferably of at least two segments, as well as a carrying plate for receiving the dental model in a removable manner in a cut-out, wherein the dental model comprises at least one tooth part, preferably at least two tooth parts, which originate(s) from a base.

In order to produce a dental prosthesis, according to a commonly used technique, a dental imprint is first made of a denture or of a portion of such a denture after a preparation has been performed beforehand by a dentist, imprint which reproduces the negative situation in the mouth of a patient. From the resulting formed negative model, a positive model is produced, which includes the area of the jaw that is to be provided with the dental prosthesis. In the case of one or more tooth stumps, the jaw area is also molded.

In order to produce a dental prosthesis on the basis of a corresponding master model, it is possible to carry out an exclusively manual manufacturing or a manufacturing in which the area in question is scanned and the resulting digitized data are used for producing dental prosthesis by the CAD/CAM method. Here it is necessary that either beforehand the model to be referred to as duplicate is severed into duplicate sections, which are then scanned individually. In order to be able to assign the duplicate sections to one another, it is necessary moreover for a correlation with the entire duplicate to be carried out. Thus, the duplicate itself and also the duplicate sections has/have to be scanned (EP-B-0 913 130).

In order to avoid these disadvantages, it is known from EP-B-1 691 712 to scan the duplicate without severing it, wherein the individual scans are assigned to one another on the basis of a referencing present on the duplicate.

A dental model can be obtained from WO-A-2010/099959, which consists of a base part with recesses and of tooth parts to be inserted therein. In order to prevent faulty insertion of tooth parts into the base part, the tooth parts comprise orienting projections.

In order to produce a master model, according to WO-A-98/10709, a carrying plate with recesses is used, carrying plate which is delimited by side surfaces having a structuring. In the bottom area of the carrying plate, bore holes are present into which the pins of segments of the model can be inserted, in order to ensure a proper positioning of the segments.

A corresponding technique can also be obtained from WO-A-01/06945. This document describes a carrying plate with tooth crowns produced by rapid prototyping. For the fastening of the tooth crowns, the carrying plate has a continuous cut-out delimited by guide grooves, in order to be able to pour foundation material through the cut-out for the fastening of the lower face of the tooth crown.

From WO-A-2007/117239, a method can be obtained for automatically producing a mold for a dental prosthesis. For this purpose, the jaw area in question is scanned intra-orally. In the process, a tooth base is formed, which has an opening for receiving a prefabricated abutment.

In WO-A-2011/103879, a computer-implemented method for generating a virtual model of a set of teeth is described, in order to produce a physical model on the basis thereof.

A carrying plate for a model is described in U.S. Pat. No. 5,506,095. The carrying plate has a cut-out with inner faces, which extends along a jaw arch, inner faces which are used as referencing, in order to allow a reinsertion of a cured mold in the cut-out. The bottom has a slit, into which an element, in particular an element made of plastic, can be inserted in order to form an intermediate layer with respect to the model and to allow easy insertion and removal from the carrying plate.

The subject matter of DE-B-10 2004 054 876 is a measuring device for 3D measurement of dental models. For this purpose, a dental model is recorded in different known rest positions. This facilitates a matching of the individual recordings.

A mold for producing a dental model is known from DE-C-197 22 989. It comprises a model plate as well as an impression tray which carries a dental imprint. The hollow space between the imprint mold and the model plate is filled with a molding material. From said molding material, sections of pins originate, which can be inserted in corresponding openings of the model plate.

In EP-A-1 520 551, a work table for dental technicians and dentists is described, which is used to produce an implant bore template.

A method for generating a computer model of a denture on the basis of digital information is the subject matter of US-A-2008/0085489.

A guide template for producing dental prostheses is described in WO-A-2008/117323. WO-A-2002/39056 relates to a surface acquisition and generation device.

In order to produce a dental prosthesis using the CAD/CAM technology, DE-A-10 2005 009 549 provides for fastening a dental model produced by a conventional method, in a base plate, using gypsum or adhesive, for example. In order subsequently to scan segments cut from the model and to match the scan data, the base plate has a referencing formed by wave geometry.

From the prior art, a method can be obtained in which a jaw area is scanned intra-orally, and on the basis of these data a dental model is produced, wherein segments of said model are fastened by means of pins in a drilled board. In order to rule out transposition of the segments, a setup plan is added to the drilled board on which the segments are to be arranged. This leads to a complicated operability and in the end it does not ensure an incorrect occupation of the drilled board.

The aim of the present invention is to further develop a method, a carrying plate as well as a dental device of the type mentioned in the introduction, in such a manner that a simple operability of the dental model is ensured, in particular ruling out a faulty insertion of the dental model or of the segments into the holder or carrying plate. At the same time, the dental model should be such that it can be produced with high precision, using the desired materials.

According to an additional aspect, it is to be ensured that the segments are fastened in a manner so that they cannot fall out, independently of their width extension in the recess or cut-out of the holder or carrying plate, wherein even frequent removal and reinsertion should not lead to any deficiencies.

According to the method, the aim is achieved essentially in that the referencing is saved in the computer and in that the at least one tooth part with the base is produced as a unit taking into consideration the referencing.

The referencing consists in particular of a structure formed by projections or indentations at least in an area of the recesses in which the base is inserted, base which is produced with the at least one tooth part as a unit, in particular by the CAM (Computer Aided Manufacturing) method.

Deviating from the known prior art, the dental model is produced with a base which has a referencing that corresponds to the holder receiving the dental model. In this manner it is ensured that after the production of the dental model, a faulty insertion into the holder is ruled out, in particular in the case where only individual segments are produced, which are then to be inserted for the production of the dental prosthesis in the holder for modeling the framework or the veneering.

The base and the tooth part are produced as a unit made from the same material, such as, for example, plastic.

A dental model usually comprises a model of the upper jaw and the lower jaw.

Therefore, the invention provides in particular for the dental model to be produced in the form of at least two adjoining segments, wherein at least one segment, preferably each segment, comprises two tooth parts with common base.

In order to prevent the segments from being capable of falling out in an uncontrolled manner, which can occur particularly with small segments, for example, segments having only a single front tooth, the invention, in an independent solution proposal, provides for the cut-out to be delimited on the underside by a bottom wall with a longitudinal slit, wherein the base on the underside is formed with a first projection for the insertion into the longitudinal slit.

The segment is prevented from falling out by the projection which is adapted to the longitudinal slit.

The secure fastening is achieved in particular, according to another independent solution proposal, if, in accordance with the teaching according to the invention, it is provided that the plate-shaped element on the upper face includes a first section which is set back relative to the surface and extends along the cut-out and transitions into said cut-out, and that the base is produced in such a manner that from said base a laterally protruding second projection originates, which is adapted to the set back first section or to an area of said first section.

As a result, the base part is in contact over a relatively large surface area with the holder, and consequently it is not,—as is the case in the prior art—attached exclusively in the cut-out itself, but is applied instead additionally by means of the laterally protruding second projection, which rests on a delimitation of the first section, which extends parallel to the surface of the holder.

The dental model itself can be a master model or a work model. The work model differs from the master model in that, in the first model, the gingival tissue is removed at the stumps to which the dental prosthesis is to be applied. This is important in order to be able to determine the preparation boundary. The possibility exists of producing segments with a preparation boundary and segments with no preparation boundary that is with gingiva. In the case where there is no gingiva contour present, a segment with concave molding is obtained. Interposing identical segments, which thus have identical stumps, results in the advantage that either a work model or a master model is available. A work model is available if a segment without gingiva is used. A master model is available if the contour of the gingiva is present.

The segments can be produced on the basis of the available digitized data of the intra-orally scanned jaw, in such a manner that said segments can be arranged in a row one after the other without sawing or cutting gap. According to the prior art, a corresponding sawing or cutting gap has a width between 0.3 mm and 0.5 mm. As a result, information is lost. According to the invention, only a minimum production-caused gap is needed, in order to ensure the insertion or the removal of the segments. The width of the segment is less than or even very much less than 0.1 mm.

A carrying plate of the above-mentioned type is characterized in that the upper face of the carrying plate has a set back area which extends along the cut-out, as second guide for the base, and/or the cut-out has, on the underside, from a slit extending along the cut-out, as third guide for the base.

Here it is provided in particular that the cut-out with the slit extends from the upper face to the lower face and continuously through the latter.

Moreover, it should be emphasized that the slit on the underside can be bridged by at least one rib extending transversely to the longitudinal direction of the slit. Here, the rib bridging the slit, wherein it is preferable for several ribs to be provided, in addition can allow a guiding or a fastening in an articulator. On the lower face of the carrying plate, one or more cut-outs or projections can be present moreover, in order to clearly fasten and attach the carrying plate in an articulator. For this purpose, a magnet can be introduced into at least one cut-out, as is usually done.

In order to facilitate, on the one hand, the insertion of the dental model or segments thereof, and, on the other hand, in order to allow a reliable guidance, the invention moreover provides for the first guide to be formed by the side surface in each case preferably having a wave geometry, with bumps and recesses extending perpendicularly to the upper face of the respective side surface, wherein, in particular, the distance between the bumps of one side surface differs from the distance between the bumps of the other side surface, in particular the distance between two bumps of the side surface extending along the outer arch is 1.5 to 10 times, preferably 2 to 5 times larger than the separation between two bumps of the opposite side surface extending along the inner arc.

Naturally, the scope of the invention is not exceeded if only one of the side surfaces that form the referencing has bumps and recesses.

A dental device of the type mentioned in the introduction is characterized in that the carrying plate on the upper face has an area set back relative to the surface thereof and extending along the cut-out, and the base has a section geometrically adapted to the area, and/or the cut-out has a bottom-side slit extending along the cut-out and the base has a projection that is geometrically adapted to the slit.

It is preferable to provide that at least one of the segments has at least two tooth parts. Here, it is provided in particular that the segments in the cut-out are arranged adjacently and that at least two tooth parts originate from a common base section.

As preferred materials for the dental model, plastics are mentioned, in particular filled plastics, particularly preferably filled polyurethane plastics.

For the holder or carrying plate, it is possible to consider using materials such as aluminum, aluminum alloys, titanium, titanium alloys, steel or plastics, without any intention of thereby delimiting the teaching according to the invention.

Additional details, advantages and features of the invention result not only from the claims, the features that can be obtained therefrom—separately and/or in combination—, but also from the following description of a preferred embodiment example that can be obtained from the drawings.

Figure 2:
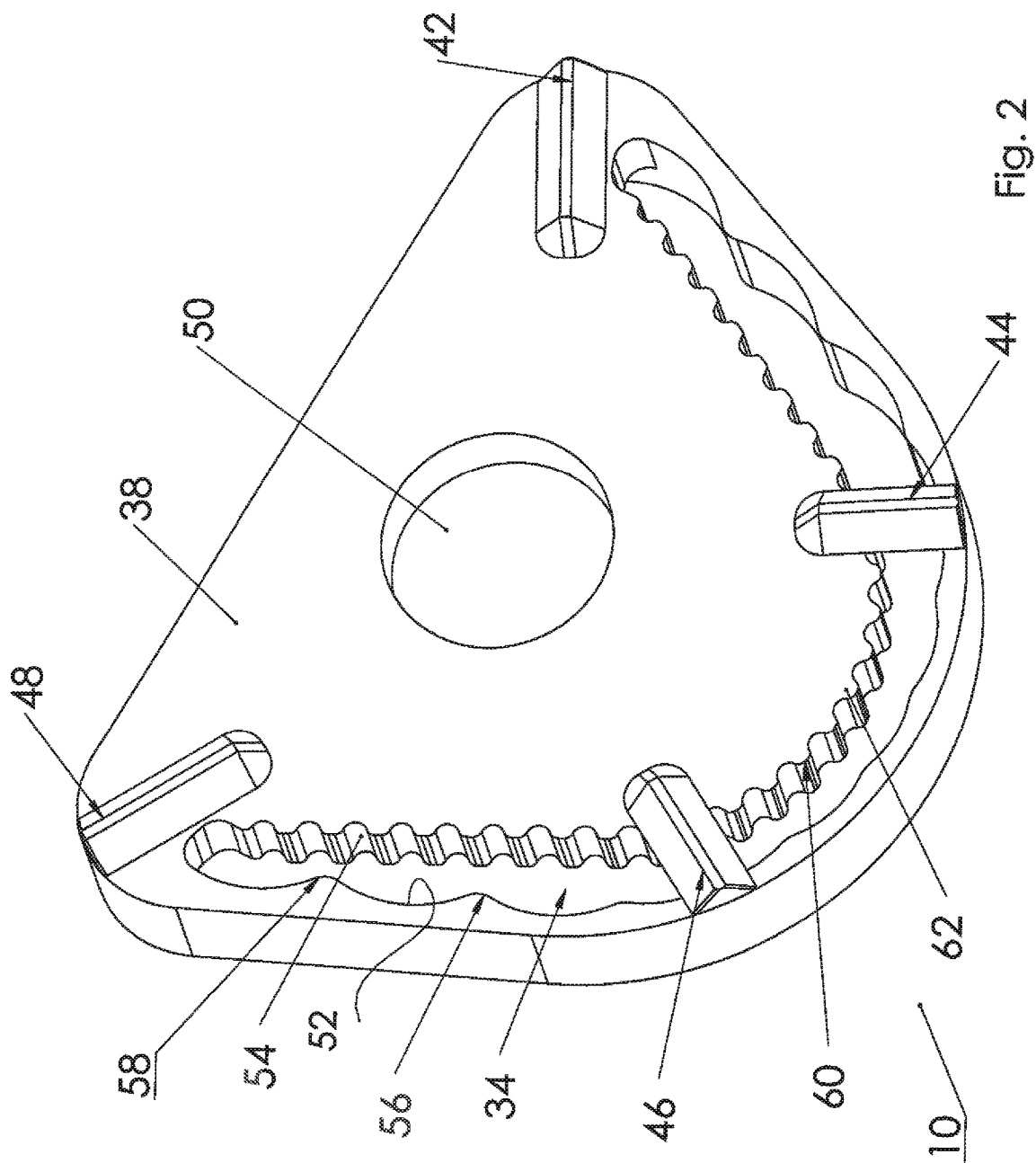
Figure 3:
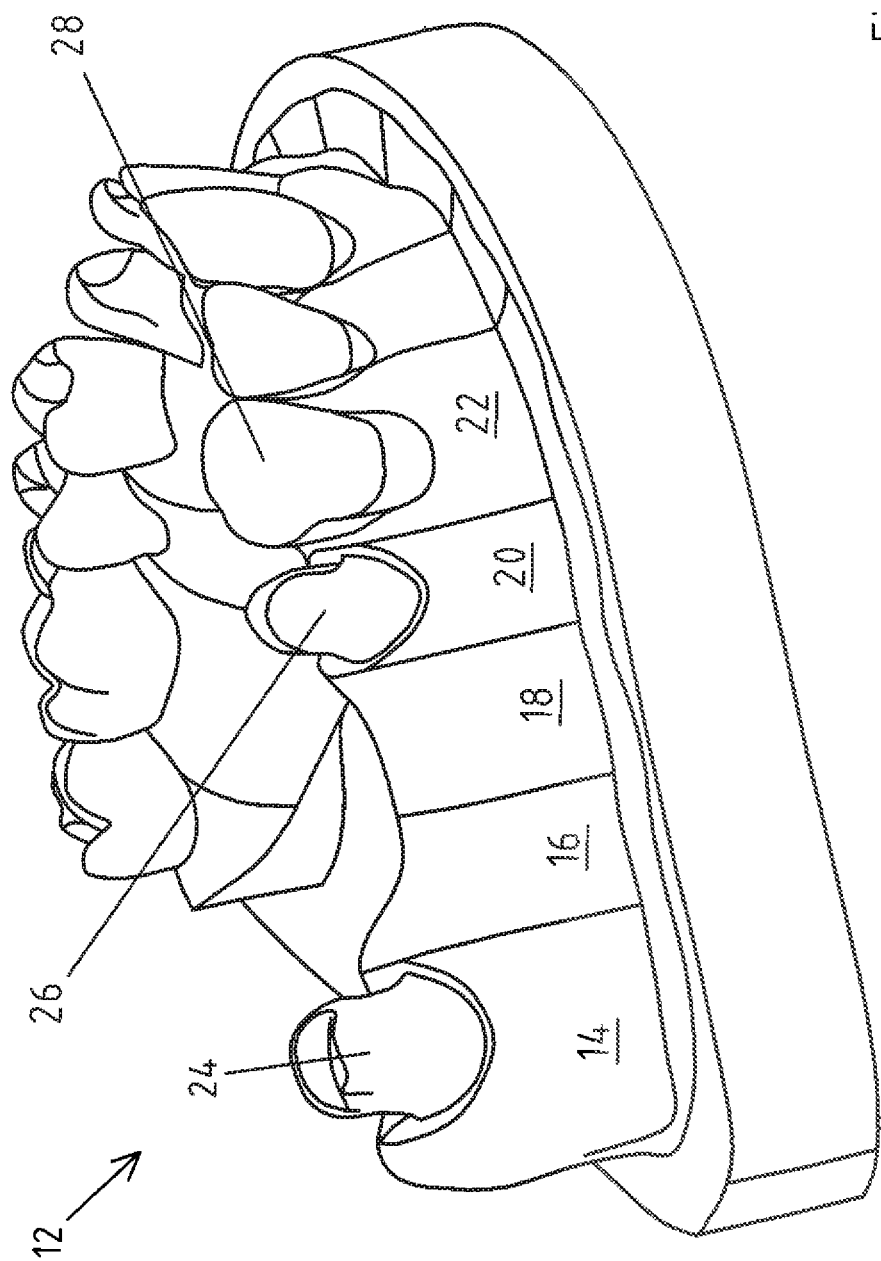
Figure 4:
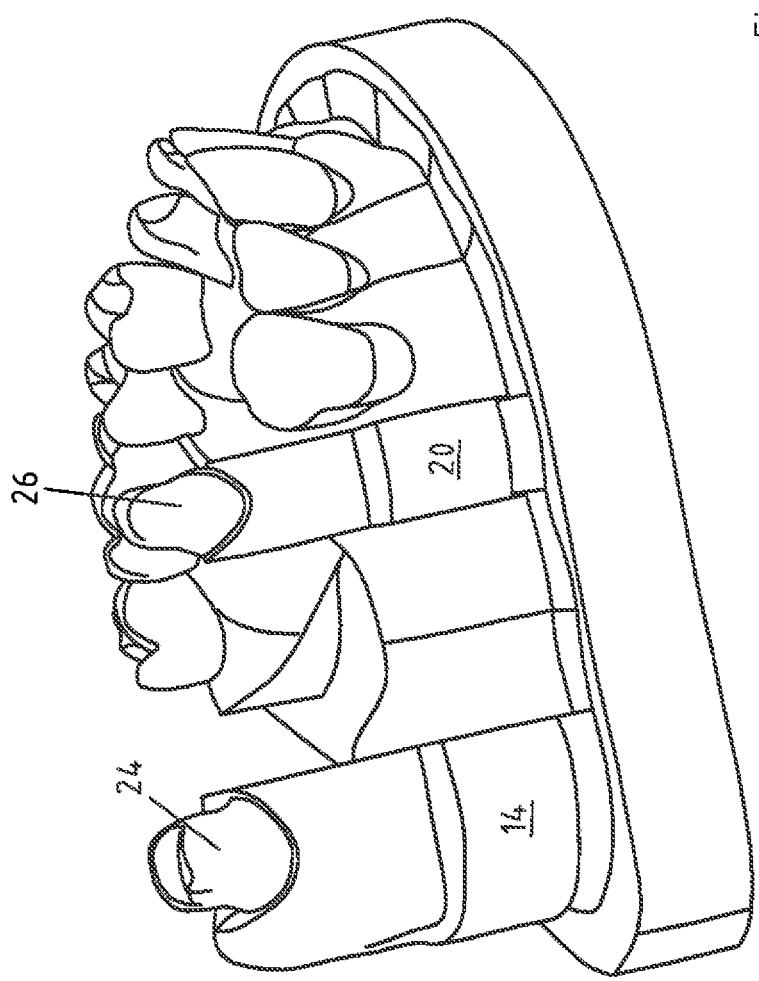
Figure 5:
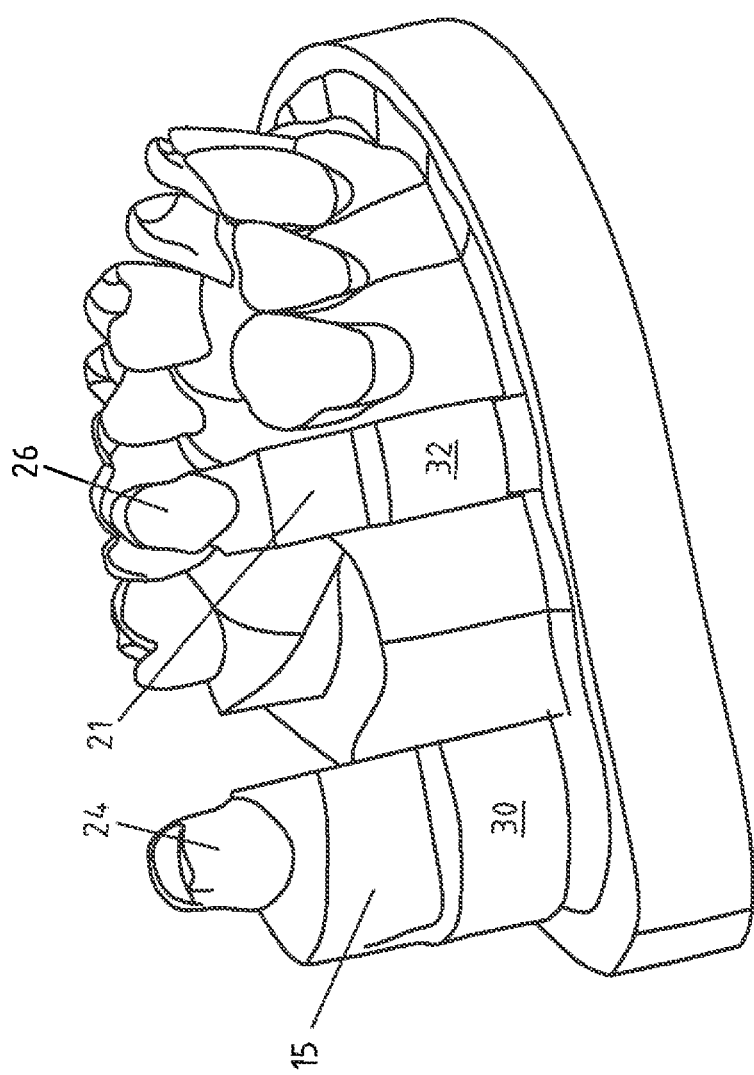
Figure 6:
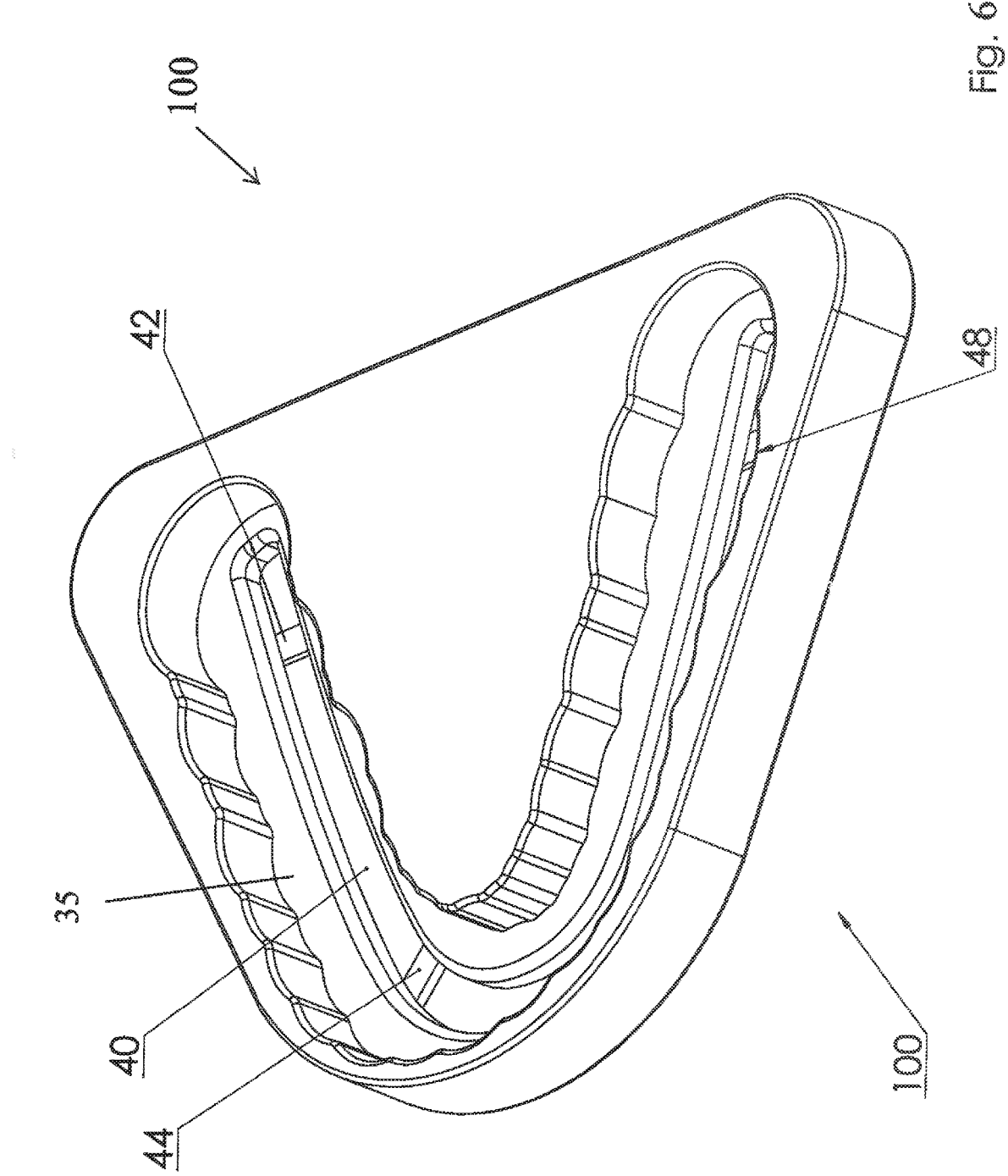
Figure 7:
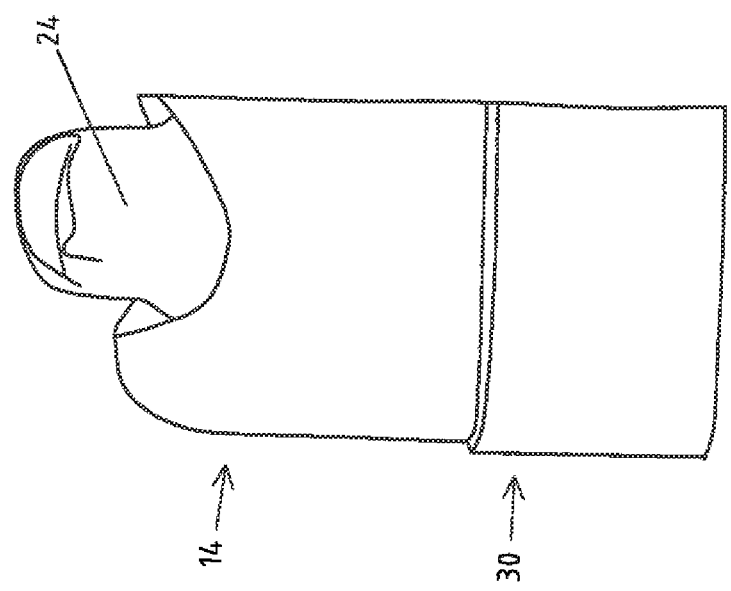
Figure 8:
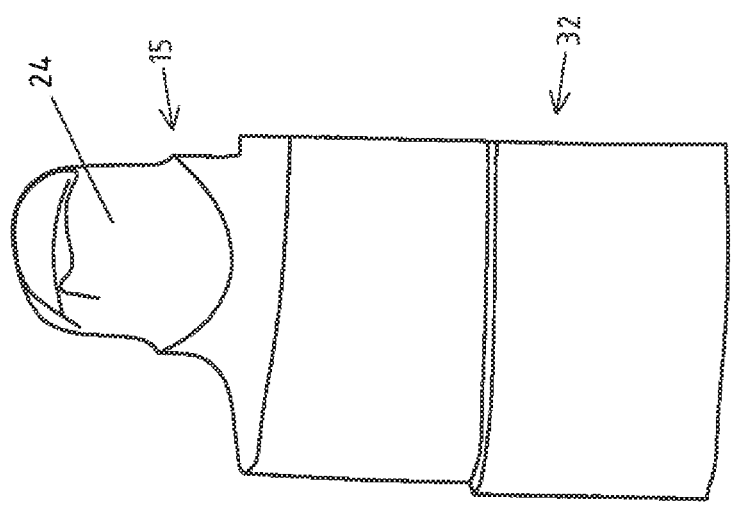

FIG. 1 shows a carrying plate for receiving a dental model from above,

FIG. 2 shows a carrying plate corresponding to FIG. 1, viewed from below, with additional ribs, FIG. 3 shows a dental model inserted in a carrying plate, which corresponds to FIGS. 1 and 2, FIG. 4 shows the dental model in the carrying plate according to FIG. 3, wherein segments which have stumps have been pulled out, FIG. 5 shows the segments having the stumps, but with concave molding, FIG. 6 shows a second embodiment of a carrying plate, FIG. 7 shows a segment without gingiva, FIG. 8 shows the segment according to FIG. 7 with gingiva, FIG. 9 shows a perspective view of a segment which is inserted in the carrying plate according to FIG. 6, FIG. 10 shows a third embodiment of a carrying plate, FIG. 11 shows a segment which is inserted in the carrying plate according to FIG. 10, and FIG. 12 shows a fourth embodiment of a carrying plate.

The drawings show basic representations of a dental model 12 which can be implemented as master model (FIG. 3, FIG. 4) or work model (FIG. 5), and which is received by a holder referred to below as carrying plate 10, 100, 200, 300. Here, the dental model 12 is cut or subdivided into segments, some of which are marked purely as examples with the reference numerals 14, 16, 18, 20, 22.

The segments 14, 20, 22 here have tooth parts 24, 26, 28, of which the parts 24, 26 are prepared and used as stumps for a receiving bridge as dental prosthesis.

Although in the depicted representation each tooth part originates from a separate segment, this is not required. In particular, it is also not required for the tooth parts that are not provided with a dental prosthesis to be segmented. Instead, several tooth parts can originate from a single segment.

For the production of the dental model 12, the jaw or jaw area of a patient, which is to be provided with a dental prosthesis, is scanned intra-orally or an imprint of the jaw or a jaw area is scanned. On the basis of the scanned data, the dental model is produced by the CAM (Computer Aided Manufacturing) method, wherein the part which protrudes over the holder 10 replicates the situation in the mouth of the patient. Here, the scanned data are recorded or matched in a known manner, since several views are required in order to scan the jaw area comprehensively or with sufficient precision. In addition, missing data or data that cannot be evaluated can be supplemented using appropriate software. However, in that regard reference is made to sufficiently known techniques.

The segments 14, 16, 18, 20, 22 can be produced individually or independently of one another according to an optimized production process. Thus, in order for the segments 14, 16, 18, 20, 22 to be inserted to the desired extent with precise positioning into the holder, and so that they can be put back simply while maintaining the original order, it is provided according to the invention to produce the tooth parts with a base 30, 32, which is adapted to a referencing present in the carrying plate 10, 100, 200, 300, as a result of which the insertion of the segments 14, 16, 18, 20, 22 with precise positioning into the carrying plate 10, 100 is ensured. The tooth part(s) with the base is (are) produced as a unit in particular from plastic.

When the term base part of a tooth part is used, this applies also to the jaw area in which no tooth is located any longer,—as in the case of the segments 16, 18—. To that extent, the meaning of tooth part must be understood to be comprehensive and it also covers an area in which only the jaw bone area with the gum tissue extends. The term tooth part must be understood to be comprehensive and it also covers artificial tooth stumps, implant posts, root extensions or the like.

As can be seen in FIGS. 1 and 2, the carrying plate 10, 100 for receiving the dental model 12 has a continuous cut-out 34—also referred to as recess—which has approximately the shape of a jaw arch, and which extends, originating from the upper face 36 of the carrying plate, to the lower face 38. While, in the embodiment examples of FIGS. 1 and 2, the recess 34 extends completely from the upper face 36 to the lower face 38 and continuously through it, in the embodiment example of FIG. 6, the cut-out 34 is delimited by a bottom wall 35 through which a slit 40 passes continuously. Naturally, the bottom wall 35 can also be closed.

In accordance with the representation of FIGS. 1, 2 and 6, the cut-out 34 extends along the lower face 38 of the carrying plate 10, 100, or the rib 42, 44, 46, 48 which bridges the slit 40, in order to ensure a sufficient dimensional stability of the carrying plate 10, 100.

In FIG. 10, a carrying plate 200 is represented, in which the cut-out 34 is delimited by a closed bottom wall 35.

The ribs 42, 44, 46, 48 can also be used for fastening, and as an aide for mounting, the carrying plate 10, 100 on an articulator. In addition, a cylindrical cut-out 50 can be provided in the bottom surface, that is to say the lower face 38, of the carrying plate 10, in order to be able to attach the carrying plate 10 in an articulator, for example, with a magnet.

A carrying plate 300 represented in FIG. 12, which basically corresponds to the carrying plate 10 according to FIGS. 1 and 2, has a longitudinal slit 99 in its base side surface 97 for fastening in an articulator. The side surface 97 is referred to as base side surface, since the carrier 300 in top view has an approximately triangular shape with rounded corners, wherein the side surface 97 comprising the longitudinal slit 99 is the base of a corresponding triangle.

The referencing of the recess 34, which is used to able to insert the dental model 12, that is to say the base thereof, or sections thereof, or base parts 30, 32 thereof which overall form the base, with precise positioning, is formed by structuring the side surfaces 52, 54, and, in particular, in the embodiment example, by a wave-shaped or tooth-shaped geometry, without any intention thereby to limit the teaching of the invention. Other suitable mechanical referencing measures can also be taken, ensuring that the segments 14, 16, 18, 20, 22 can be inserted in a single position and thus unequivocally in the cut-out 34.

In accordance with the representations depicted in FIGS. 1 and 2, the delimitations of the side walls 52, 54 differ in that the distance between the bumps 56, 58 of the side surface 52 of the recess or cut-out 34, which extends along the outer arch, is greater than the distance between the bumps 60, 62 of the side surface 54 of the inner arc, which extends internally, wherein, in particular, the distance between two to four bumps 60, 62 of the inner surface 54 should be equal to the distance between two successive bumps 56, 58 of the external inner surface 52.

In the embodiment example of FIG. 10, the carrying plate 200, in its side walls 52, 54, in each case has a wave structure, which, in reference to the distance between the bumps, is approximately identical, without the required individualization being lost, which is required for the tooth parts to be insertable in a unique unequivocal position in the recess 34 and thus the carrying plate 200.

If the structures, that is to say the wave-shaped pattern of the side delimitations, namely the inner surfaces 52, 54 of the recess or cut-out 34, offer the possibility of an unequivocal positioning of the segments 14, 16, 18, 20, 22, in that the base parts 30, 32 are structured correspondingly, then it is ensured by means of the longitudinal slit 40 that an undesired falling out of the segments does not occur, particularly in the front tooth area, that is to say in the area of the jaw having the smallest fitting area with the largest curvature. For this purpose, the base parts have projections—also referred to as first projections—which are adapted to the geometry of the longitudinal slit 40, and which are indicated in FIG. 6 and marked with the reference numeral 64.

Based on FIG. 11, it becomes clear that a base 68 having a tooth part 66, and which is also referred to as base part, can consist of a lower section 70, a central section 72, and an upper section 74 which transitions into the jaw area with the tooth 66, wherein the geometry thereof is or the geometries thereof are determined on the basis of the digitized data obtained by scanning.

The lower section 70 of the base part 68 is inserted in the recess 34. One can see that the front surface of the lower section 70 of the base part 68, which is shown in the representations of FIG. 11, has a wave geometry which corresponds to that of the internal inner surface 54 of the cut-out 34 of FIGS. 1, 2. In contrast, the rear surface of the lower section 70 of the base part 68 is designed to be more flat, since the wave geometry of the external inner surface 52 is spread out, as FIGS. 1, 2 illustrate.

The central section 72 lies on the upper face 36 of the carrying plate 10, in particular in a set back area 82, as can be seen in FIGS. 1, 12. The set back area 82 is referred to as first section. The result of this is a large-area contact of the base part 68 on the carrying plate 10, 300, as a result of which the segment is prevented from falling out, in particular to such an extent that optionally the slit 40 and the projection 64 (FIG. 9) which is adapted to said slit, on the lower face of the lower section of the base part 68, can be dispensed with.

Independently thereof, the slit 40 should extend in the center between the side surfaces 52, 54. The slit 40 then has, if it passes continuously through the bottom wall 35, mutually parallel walls. If the slit 40 is formed substantially as a groove, then it should have a U or V shape in cross section.

Moreover, regarding the lateral surfaces or inner surfaces 52, 54, it should be noted that they extend perpendicularly to the upper and lower face 36, 38.

Both the referencing produced by the structuring of the inner or lateral surfaces 52, 54 of the recess or cut-out 34 and also the geometry of the set back area 82 in the upper face 36 of the carrying plate 10 and—to the extent present—the shape and the geometry of the slit 62 are saved as data in a computer in which the tooth and jaw data obtained by intra-oral scanning or scanning of an imprint are also saved. The corresponding data are then linked in order to be supplied to a processing machine for the purpose of producing the dental model 12, i.e., the segments 14, 16, 18, 20, 22 thereof. Conventional machining procedures, for example, by rotary milling of a blank, are carried out by means of the machining apparatus, in order to produce the segments 14, 16, 18, 20, 22. Here, said segments can have a geometry such that there is no cutting or sawing gap between the segments 14, 16, 18, 20, 22, which is necessarily obtained in models produced in other ways. A pseudo-sawing cut can also be generated intentionally.

Independently thereof, the segments 14-22, if they are inserted in the cut-out 34, should have a gap A of less than or much less than 0.1 mm.

It should be mentioned that not only the lower face 73 of the central section 72 bears against the surface of the section 82 of the set back carrying plate 10, but external free delimitation surface 74, which extends perpendicularly to the lower face 73 of the central section 72, also bears against the set back wall 75 of the area 82, which forms a step toward the upper face 36.

The set back section or area 82 not only forms a guide for the base or a section of the base of the segment, but it also facilitates the removal of the segment from the cut-out 34. As a result of the relatively large extent of the central section 72 which extends substantially perpendicularly to the cut-out, it is possible, in the case in which a force is applied to the upper part 74, to make use of a lever action due to the extent of the central section 72, as a result of which the lower section 70 of the base 68, which is inserted fitting perfectly into the cut-out 34, can be removed from the cut-out 34.

The segment which can be seen in FIG. 9 is inserted in the carrying plate or holder 100 according to FIG. 6. One can see that the rib 64, which is adapted to the geometry of the slit 40 in the carrying plate 100, is inserted in the recess 34 from the lower face of the base or the lower section 70 thereof.

A comparison of FIGS. 3 and 4 shows a situation in which the segments 14 and 20, which have the stumps 24, 26, are to be removed from the recess 34 of the carrying plate 10, or inserted in them. Here, the segments 14, 20 with the additional segments form a master model, wherein the actual contour of the gingiva is present.

However, in order to determine the preparation boundary, along which the dental prosthesis which is not represented extends, a possibility exists also based on the scan, of producing the stumps 24, 26 without gingiva, so that, if appropriate segments 15, 21 are used, which match the segments 14, 20 identically in terms of their base parts 30, 32, a work model with concave molding present beneath the tooth stumps 24, 26 is obtained, as a result of which the preparation boundary is visible.

From a corresponding work model, the tooth construction is then prepared by manual shaping or by direct use of the scan data for producing a framework by a CAD/CAM method. The latter possibility should be given preference. Subsequently, the corresponding framework is placed onto the tooth stumps 24, 26, wherein, however, the segments 15, 21 are replaced by the segments 14, 20 which have the gingiva. Consequently, the master model is used again. This is necessary in order to determine whether the reconstructions enclose the teeth stumps 24, 26 fitting perfectly up to the gingiva. Subsequently, using the usual technique, a veneering of the framework is carried out.

Independently thereof, it should be noted that the term framework should be understood very broadly, that is to say it refers not only to bridge frameworks, but also to crowns, onlays, inlays or other tooth reconstructions. To that extent, the term framework should be understood as a synonym.

In FIGS. 7 and 8, the segments 14 and 15 are shown again quite generally. One can see that the segment 14 in regard to its tooth stump 24 is enclosed by the gingiva, wherein the tooth stump 24 of the segment 15 comprises a concave molding that is the gingiva has been removed.

The base parts 30, 32 of the segments 14, 15 are identically matching, so that a placement of the segments 14, 15 can occur at only one and the same site of a carrying plate. This is ensured by the referencing of the corresponding cut-out 34 in the carrying plate 10, 100, 200, 300, which is reproduced in the base sections 30, 32 in accordance with the positions that the segments 14, 15 are to assume.

On the basis of the teaching according to the invention, for the first time, a dental model is made available by means of which, during the preparation, a base part is automatically also formed at the same time, which has a referencing that corresponds to a carrying plate—which can also be referred to as a holding plate or holder—, so that an unequivocal positioning is ensured. Consequently, the user is able to insert the segments without further instruction, since only a single positioning possibility exists for each segment.

With regard to the referencing, it should be noted that other geometries than the described wave geometry can also be considered. Basically, any desired structures can be considered, provided there are no abrupt changes in direction, such as jags, for example, which would unnecessarily complicate production by an ablating method, such as milling.

Advantages of the invention can also be obtained from the following. Thus, a dentist can scan a jaw and then have individual segments produced on the basis of these data. Segments whose production has been outsourced, for example, are then made available to the dentist or dental technician, who can insert the segments without problem into a holder available to him/her, in particular on the basis of the design of the base according to the invention with predetermined referencing which the holder has in its recess. In addition, the segments can have an optically detectable referencing, such as a numbering, in order to avoid testing the insertion into the recess. By means of an appropriate optical marking, such as numbering, the rough alignment of the segments with the cut-out in the holder is facilitated. The precise insertion is ensured by the referencing—that is the mechanical structure—on the base and the associated referencing of the cut-out in the holder.

The invention claimed is:

1. A carrying plate for receiving a denture model, or a segment or several segments of such a denture model, wherein the denture model, or at least one segment of said model, has a base comprising a tooth part, and wherein the carrying plate has an upper and a lower face, and a cut-out extending along an arc, with side surfaces comprising a referencing which forms a first guide for the base, wherein the base and the tooth part are manufactured as a unit from the same material,
wherein the upper face of the carrying plate has a set-back area extending along the cut-out, as a second guide for the base, and the cut-out has a slit extending along the cut-out, as a third guide for the base.

2. The carrying plate according to claim 1, wherein the slit is formed in a bottom wall of the cut-out, or passes continuously through the bottom wall of the cut-out.

3. The carrying plate according to claim 2, wherein the cut-out comprises a V-shaped or U-shaped cross section.

4. The carrying plate according to claim 1, wherein an underside of the slit is bridged by at least one rib which extends transversely to the longitudinal direction of the slit.

5. The carrying plate according to claim 4, wherein the at least one rib is a guide and/or a fastening for an articulator.

6. The carrying plate according to claim 1, wherein the first guide is formed by the side surfaces, each having a wave geometry, with bumps and indentations extending perpendicularly to the upper face.

7. The carrying plate according to claim 6, wherein a distance between the bumps of one side surface differs from a distance between the bumps of the other side surface.

8. The carrying plate according to claim 7,
wherein the side surfaces comprise an inner side surface and an opposing outer side surface; and
wherein the distance between two bumps of the outer side surface is 1.5 to 10 times greater than the distance between two bumps of the inner side surface.

9. The carrying plate according to claim 7,
wherein the side surfaces comprise an inner side surface and an opposing outer side surface; and
wherein the distance between two bumps of the outer side surface is 2 to 5 times greater than the distance between two bumps of the inner side surface.

10. The carrying plate according to claim 1, wherein the arc has a configuration of a dental arch.

11. A dental device comprising a dental model and a carrying plate which receives the dental model in a removable manner in a cut-out having side surfaces, wherein the dental model has at least one tooth part originating from a base, and the tooth part and the base are manufactured as a unit from the same material,
wherein the carrying plate has, on an upper face thereof, an area which is set back with respect to the surface of said carrying plate, and which extends along the cut-out, and the base comprises a section which is adapted geometrically to the area, and the cut-out comprises a slit which extends on a bottom face along the cut-out, and the base comprises a projection which is adapted geometrically to the slit.

12. The dental device according to claim 11, wherein the dental model includes at least two segments that are arranged one after the other in the cut-out, wherein each segment comprises a base and at least one tooth part, and wherein at least two tooth parts originate from the base of one of the at least two segments.

13. The dental device according to claim 12, wherein the segments inserted in the carrying plate have a gap A, where A is less than 0.1 mm.

14. The dental device according to claim 13, wherein A is less than 0.1 mm.

15. The dental device according to claim 12, wherein the segments are produced by the CAM method.

16. The dental device according to claim 11, wherein the dental model further comprises at least two segments.

17. The dental device according to claim 11, wherein the dental model has at least two tooth parts originating from the base.

* * * * *